US010914659B2

(12) United States Patent
Kshirsagar et al.

(10) Patent No.: US 10,914,659 B2
(45) Date of Patent: *Feb. 9, 2021

(54) GUANIDINE-FUNCTIONALIZED METAL SILICATE PARTICLES AND METHODS OF MAKING AND USING SUCH PARTICLES

(71) Applicant: 3M INNOVATIVE PROPERTIES COMPANY, St. Paul, MN (US)

(72) Inventors: Manjiri T. Kshirsagar, Woodbury, MN (US); George W. Griesgraber, Eagan, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/914,017

(22) PCT Filed: Jun. 4, 2014

(86) PCT No.: PCT/US2014/040861
§ 371 (c)(1),
(2) Date: Feb. 24, 2016

(87) PCT Pub. No.: WO2015/047464
PCT Pub. Date: Apr. 2, 2015

(65) Prior Publication Data
US 2016/0209305 A1 Jul. 21, 2016

Related U.S. Application Data

(60) Provisional application No. 61/884,254, filed on Sep. 30, 2013.

(51) Int. Cl.
| | |
|---|---|
| *G01N 1/40* | (2006.01) |
| *C12Q 1/24* | (2006.01) |
| *C01B 33/20* | (2006.01) |
| *C01B 33/22* | (2006.01) |
| *C01B 33/26* | (2006.01) |
| *B01D 39/06* | (2006.01) |
| *C07F 7/10* | (2006.01) |
| *D04H 13/00* | (2006.01) |

(52) U.S. Cl.
CPC .......... *G01N 1/4077* (2013.01); *B01D 39/06* (2013.01); *C01B 33/20* (2013.01); *C01B 33/22* (2013.01); *C01B 33/26* (2013.01); *C07F 7/10* (2013.01); *C12Q 1/24* (2013.01); *D04H 13/00* (2013.01); *D10B 2403/02421* (2013.01); *G01N 2001/4088* (2013.01); *G01N 2333/245* (2013.01)

(58) Field of Classification Search
CPC ........ G01N 1/4077; G01N 2001/4088; G01N 2333/245; C12Q 1/24; C01B 33/20; C01B 33/22; C01B 33/26; B01D 39/06; C07F 7/10; D04H 13/00; D10B 2403/02421
See application file for complete search history.

(56) References Cited

U.S. PATENT DOCUMENTS

| | | | |
|---|---|---|---|
| 5,147,927 A * | 9/1992 | Baghdachi | C08G 18/10 524/710 |
| 6,031,119 A | 2/2000 | Lee | |
| 6,045,913 A | 4/2000 | Castle | |
| 6,808,908 B2 | 10/2004 | Yao | |
| 7,125,488 B2 | 10/2006 | Li | |
| 9,657,038 B2 * | 5/2017 | Griesgraber | C07F 7/1836 |
| 2002/0011447 A1 | 1/2002 | Waldmann | |
| 2003/0022216 A1 * | 1/2003 | Mao | G01N 33/5306 435/6.13 |
| 2003/0100086 A1 | 5/2003 | Yao | |
| 2003/0152759 A1 | 8/2003 | Chao | |
| 2003/0217963 A1 | 11/2003 | Mitchell | |
| 2005/0247608 A1 | 11/2005 | Collias | |
| 2005/0279696 A1 | 12/2005 | Bahm | |
| 2006/0134595 A1 | 6/2006 | Rapp | |
| 2009/0204087 A1 | 8/2009 | Herfert | |
| 2010/0297053 A1 | 11/2010 | Hirukawa | |
| 2011/0217752 A1 | 9/2011 | Rasmussen | |
| 2012/0058505 A1 * | 3/2012 | Helms | B82Y 15/00 435/29 |
| 2012/0276580 A1 | 11/2012 | Kshirsagar | |

(Continued)

FOREIGN PATENT DOCUMENTS

| | | |
|---|---|---|
| CN | 102317523 | 1/2012 |
| CN | 102453273 | 5/2012 |
| JP | 2010-201307 | 9/2010 |

(Continued)

OTHER PUBLICATIONS

Beaurepaire, E et al. Nano Letters. 2004. 4(11): 2079-2083.*
'1-Propanamine, 3-(triethoxysilyl)-.' NIST Chemistry WebBook. 2017. [online]. [retrieved on Nov. 14, 2017]. Retrieved from the Internet <URL: http://webbook.nist.gov/cgi/cbook.cgi?ID=C919302&Mask=200>. (Year: 2017).*
'N-(2-Aminoethyl)-3-aminopropyltrimethoxysilane.' NIST Chemistry WebBook. 2017. [online]. [retrieved on Nov. 14, 2017]. Retrieved from the Internet <URL: http://webbook.nist.gov/cgi/cbook.cgi?ID=1760-24-3>. (Year: 2017).*

(Continued)

*Primary Examiner* — Renee Claytor
*Assistant Examiner* — Susan E. Fernandez
(74) *Attorney, Agent, or Firm* — Adrian L. Pishko (57) ABSTRACT

Guanidine-functionalized particles and methods of making and using such particles are provided, such as guanidine-functionalized metal silicate particles. A nonwoven article is also provided including a porous fibrous nonwoven matrix and guanidine-functionalized metal silicate particles enmeshed within the porous fibrous nonwoven matrix. The nonwoven article may be used, for instance, for removing microorganisms from an aqueous sample by contacting a fluid sample with the nonwoven article such that at least a portion of the microorganisms are removed from the fluid sample.

22 Claims, 1 Drawing Sheet

(56) References Cited

U.S. PATENT DOCUMENTS

2015/0307526 A1* 10/2015 Griesgraber .......... C07F 7/1836
   435/183

FOREIGN PATENT DOCUMENTS

| WO | WO 2009-085357 | 7/2009 | | |
|----|----------------|--------|---|---|
| WO | WO 2010/074773 | 7/2010 | | |
| WO | WO 2012-001142 | 1/2012 | | |
| WO | WO 2012-078426 | 6/2012 | | |
| WO | WO 2012078426 A2 * | 6/2012 | ............ | C12M 47/02 |
| WO | WO 2014-088807 | 6/2014 | | |

OTHER PUBLICATIONS

Noshay, A et al. Silylamine-hydroxyl reaction in the synthesis of organo-siloxane block copolymers. Ind. Eng. Chem. Prod. Res. Develop. 1973. 12(4): 268-277. (Year: 1973).*

Voronkov, MG. The third route to the formation of the Si—O—Si-group and siloxane structures. To siloxanes through silanones. Journal of Organometallic Chemistry. 1998. 557: 143-155. (Year: 1998).*

3M Cosmetic Microspheres CM-111 Product Information, 2005, 2 pages.

Blanc, "The Preparation and Use of Novel Immobilised Guanidine Catalysts in Base-Catalysed Epoxidation and Condensation Reactions", Green Chemistry, 2000, vol. 2, pp. 283-288.XP002729545.

Faria, "Tetramethylguanidine Covalently Bonded onto Silica Gel Surface as an Efficient and Reusable Catalyst for Transesterification of Vegetable Oi", Applied Catalysis A: General, 2008, vol. 338, pp. 72-78.XP26130229.

Kim, "Preparation of Guanidine Bases Immobilized on SBA-15 Mesoporous Material and their Catalytic Activity in Knoevenagel Condensation", Studies of Surface Science and Catalysis, 2003, vol. 146, pp. 505-508, XP9104595.

Kramer, "Guanidinium Functionalised Silica-based Anion Exchangers Significantly Improve the Selectivity of Platinum Group Metal Recovery from Process Solutions", Separation and Purification Technology, 2006, vol. 49, pp. 181-185, XP28035321.

International Search Report for PCT International Application No. PCT/US2014/040861, dated Oct. 6, 2014, 4 pages.

Pena-Alonso et al., "Study of the hydrolysis and condensation of c-Aminopropyltriethoxysilane by FT-IR spectroscopy," J. Mater Sci (2007) 42:595-603.

* cited by examiner

GUANIDINE-FUNCTIONALIZED METAL SILICATE PARTICLES AND METHODS OF MAKING AND USING SUCH PARTICLES

CROSS REFERENCE TO RELATED APPLICATIONS

This application is a national stage filing under 35 U.S.C. 371 of PCT/US2014/040861, filed Jun. 4, 2014, which claims priority to U.S. Application No. 61/884,254, filed Sep. 30, 2013, the disclosure of which is incorporated by reference in its/their entirety herein.

BACKGROUND

Microbial removal for purposes such as purification, isolation, detection, and the like, has long been an objective of investigators.

SUMMARY

In broad summary, herein are disclosed guanidine-functionalized metal silicate particles and methods of making and using such particles.

In a first aspect, the present disclosure provides a guanidine-functionalized metal silicate particle. The guanidine-functionalized metal silicate particle includes a metal silicate particle that is modified with at least one silane reagent having the formula $X_{3-n}R^a{}_n Si$—Y-G, wherein: n is 0, 1, or 2; each $R^a$, if present, is independently an alkyl, aralkyl, or aryl; Y is a divalent group comprising an alkylene having 2 to 20 carbons; G is a guanidine group of the formula —NH—C(=NH)—NH$_2$; and each X is independently alkoxy or acyloxy.

In a second aspect, the present disclosure provides a method of making guanidine-functionalized metal silicate particles. The method includes: (a) reacting an O-methylisourea salt with a linker comprising the formula $X_{3-n}R^a{}_n Si$—Y—NH$_2$, wherein: n is 0, 1, or 2; each $R^a$, if present, is independently an alkyl, aralkyl, or aryl; Y is a divalent group comprising an alkylene having 2 to 20 carbons; and each X is independently alkoxy or acyloxy, to form a guanidine-functionalized linker; and (b) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

In a third aspect, the present disclosure provides a nonwoven article. The nonwoven article includes: (a) a porous fibrous nonwoven matrix; and (b) a plurality of guanidine-functionalized metal silicate particles according to the first aspect of the present disclosure. The plurality of guanidine-functionalized metal silicate particles is enmeshed within the porous fibrous nonwoven matrix.

In a fourth aspect, the present disclosure provides a method of removing microorganisms from an aqueous sample. The method includes: (a) providing a nonwoven article according the third aspect of the present disclosure; (b) providing a fluid sample containing at least one microorganism strain; and (c) contacting the nonwoven article with the fluid sample such that at least a portion of the at least one microorganism strain is removed from the fluid sample.

In a fifth aspect, the present disclosure provides a method of making a nonwoven article according to the third aspect of the present disclosure. The method includes: (a) providing a plurality of fibers; (b) providing a plurality of guanidine-functionalized metal silicate particles according to the first aspect of the present disclosure; and (c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix.

In a sixth aspect, the present disclosure provides a filtration device. The filtration device includes a container having inlet and outlet ports for liquid passage, and a nonwoven article according to the third aspect of the present disclosure contained within the container.

In some embodiments of any of the above aspects of the present disclosure, the guanidine-functionalized metal silicate particle is a guanidine-functionalized magnesium silicate particle; in some embodiments, the guanidine-functionalized metal silicate particle is amorphous; and in some embodiments, the guanidine-functionalized metal silicate particle is an amorphous guanidine-functionalized magnesium silicate particle. In some embodiments of any of the above aspects of the present disclosure, the guanidine-functionalized metal silicate particle is a guanidine-functionalized aluminum silicate particle; in some embodiments, the guanidine-functionalized metal silicate particle is amorphous; and in some embodiments, the guanidine-functionalized metal silicate particle is an amorphous guanidine-functionalized aluminum silicate particle.

These and other aspects of the invention will be apparent from the detailed description below. In no event, however, should the above summary be construed to limit the claimable subject matter, whether such subject matter is presented in claims in the application as initially filed or in claims that are amended or otherwise presented in prosecution.

DETAILED DESCRIPTION

Figure 1:
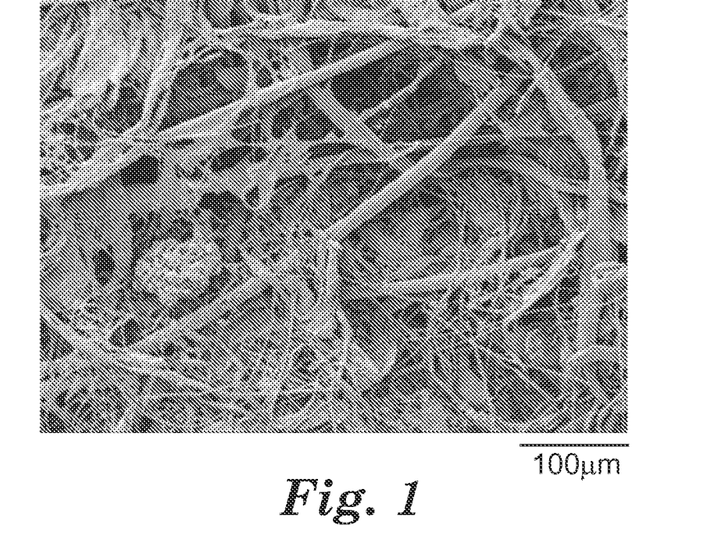
FIG. 1 is the scanning electron micrograph (SEM) of guanidine-functionalized aluminum silicate particles in a fibrous nonwoven matrix, prepared as described for Example E3.
Figure 2:
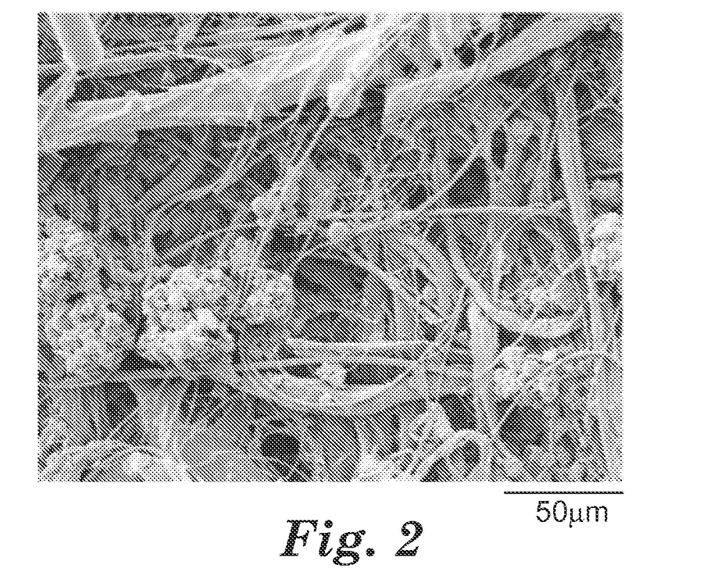
FIG. 2 is the scanning electron micrograph of FIG. 1 at a different magnification.

In the following detailed description, various sets of numerical ranges (for example, of the number of carbon atoms in a particular moiety, of the amount of a particular component, or the like) are described, and, within each set, any lower limit of a range can be paired with any upper limit of a range. Such numerical ranges also are meant to include all numbers subsumed within the range (for example, 1 to 5 includes 1, 1.5, 2, 2.75, 3, 3.80, 4, 5, and so forth).

As used herein, the term "and/or" means one or all of the listed elements or a combination of any two or more of the listed elements.

The words "preferred" and "preferably" refer to embodiments of the present disclosure that may afford certain benefits under certain circumstances. Other embodiments may also be preferred, however, under the same or other circumstances. Furthermore, the recitation of one or more preferred embodiments does not imply that other embodiments are not useful, and is not intended to exclude other embodiments from the scope of the invention.

The term "comprises" and variations thereof do not have a limiting meaning where these terms appear in the description and claims.

As used herein, "a," "an," "the," "at least one," and "one or more" are used interchangeably.

As used in this patent application:

"enmeshed" (in regard to particles in a fibrous nonwoven matrix) means that the particles are entrapped in the fibrous nonwoven matrix (and, preferably, distributed within it), rather than merely being borne on its surface;

"fibrillated" (in regard to fibers or fibrous material) means treated (for example, by beating) in a manner that forms fibrils or branches attached to a fiber's main trunk;

"fibrous nonwoven matrix" means a web or medium, other than a woven or knitted fabric, comprising interlaid fibers (for example, a web comprising fibers that are interlaid by meltblowing, spunbonding, or other air laying techniques; carding; wet laying; or the like);

"microorganism" means any cell or particle having genetic material suitable for analysis or detection (including, for example, bacteria, yeasts, viruses, and bacterial endospores);

"microorganism strain" means a particular type of microorganism that is distinguishable through a detection method (for example, microorganisms of different genera, of different species within a genus, or of different isolates within a species);

"sample" means a substance or material that is collected (for example, to be analyzed);

"sample matrix" means the components of a sample other than microorganisms;

"target cellular analyte" means any cellular analyte that is desired to be detected; and "through pore" (in reference to a porous matrix) means a pore that comprises a passageway or channel (with separate inlet and outlet) through the porous matrix.

A nonwoven article of the present disclosure includes a fibrous nonwoven matrix and particles enmeshed within the fibrous nonwoven matrix. The fibrous nonwoven matrix includes pores which allow liquid to flow through the nonwoven article and to contact the enmeshed particles.

The particles are guanidine-functionalized metal silicate particles. A guanidine-functionalized metal silicate particle comprises at least one guanidine-containing ligand. The guanidine-containing ligand is formed by modifying the metal silicate particle with a guanidine-containing silane having the structure shown in Formula 1:

Formula 1

In Formula 1, Si is a silicon atom, and G denotes a guanidine group of the formula —NH—C(=NH)—NH$_2$. Y is a divalent group that is covalently bonded to the silicon atom at one end and to the G group at the other end. Each R$^a$ group, if any are present, is independently an alkyl, aralkyl, or aryl group, and is attached to the silicon atom. Each X is a leaving group covalently bonded to the silicon atom and is independently alkoxy or acyloxy, and n is 0, 1, or 2.

A typical alkylene can be up to 20, up to 16, 12, 10, 8, 7, 6, 5, 4, or even up to 3 carbons, or even 2 carbons, inclusive of the terminal atoms of the divalent group. In some embodiments, Y is a divalent group comprising an alkylene of 3 to 6 carbons. In a preferred embodiment, Y is a divalent group having 3 carbons (i.e., propyl).

In Formula 1, each leaving group X is independently an alkoxy group of 1, 2, 3, 4, 5, 6, 7, 8, 9, or even up to 10 carbons, or is an acyloxy group of 2 carbons, or 3, 4, 5, 6, 7, 8, 9, or even up to 10 carbons, where the alkoxy or acyloxy group is bonded to the silicon through an oxygen atom.

In some embodiments, n is 0. When n is 0, no R$^a$ groups are present, and Formula 1 can be re-written more simply as shown in Formula 2 (where Si, G, Y, and X are as defined for Formula 1):

Formula 2

When the silane of Formula 1 (or Formula 2) reacts with an —OH group on the surface of a metal silicate particle, at least one X leaving group is replaced by a covalent bond of between the silicon atom and an oxygen atom on the surface of the metal silicate particle. An embodiment of a guanidine-functionalized metal silicate particle comprising a specific exemplary guanidine-containing ligand within the general type represented by Formula 1, wherein n=0 (i.e., as in Formula 2), is shown in Formula 3 (the circle in Formula 3 represents a metal silicate particle):

Formula 3

It will be understood that Formula 3 represents a specific embodiment wherein n is 3 and Y is a divalent group that is alkylene having 3 carbons. In each of Formulas 1 to 3, the ionization state of the guanidine group is omitted; however, it will be understood that in various environments such guanidine groups may be charged or uncharged (e.g., protonated or deprotonated), for example, according to the pH of a liquid medium in which the guanidine group is present, as discussed later herein.

The covalent bond(s) between the oxygen(s) of the ligand and the particle can be conveniently obtained, for example, by reacting a Si-bonded hydrolyzable group of the guanidine-containing precursor with a hydroxyl group of the particle, as discussed in detail later herein. While the exemplary structure of Formula 3 shows three such bonded oxygen atoms (i.e., n=3 in Formula 1), it will be appreciated that in various embodiments one, two or three such bonded oxygen atoms can be provided. If less than three such oxygen atoms are bonded to the silicon atom, other substituents (e.g., substituents that are not bonded to the particle, and which are not shown in Formula 1) may be present on the silicon atom. For example, the guanidine-containing ligand can include a polymeric structure involving formation of Si—O—Si (i.e., siloxane) groups, resulting from Si—O bonds being formed between two or more guanidine-containing ligand precursors. Without being bound by theory, it is thought that Si—O—Si groups may form in the presence of added water, or other aqueous solvents, or other agent that can hydrolyze bonds in Si—O—R groups, to give rise to more complex guanidine-containing ligand structures attached to particles, including such possible structures as shown in the non-limiting examples of Formulas 4a to 4d (each R in Formulas 4a to 4d independently being H or lower alkyl (e.g., methyl), or even another Si atom in which may or may not be attached to the metal silicate particle through an Si—O— bond; the circle in each of Formulas 4a to 4d represents a metal silicate particle):

Formula 4a

Formula 4b

Formula 4c

Formula 4d

It is seen from Formulas 4a to 4d that a network of polymerized guanidine-containing ligands can form a coating on the surface of the metal silicate particle. In some embodiments it may be desirable to obtain the particle functionalized with polymerized guanidine-containing ligand (e.g., as in any of the non-limiting polymerized guanidine-containing ligand structures shown in Formulas 4a to 4d, or the like, having at least one Si—O—Si group in the polymerized guanidine-containing ligand), as a means of increasing the loading of nitrogen-containing guanidine groups on the surface of the metal silicate particle. It is thought that in at least these types of polymerizations, a loading of nitrogen-containing guanidine groups on the surface of the metal silicate particle can attain levels of surface nitrogen content in a range from 1 to 10 atomic percent, as can be measured, for example, by X-ray photoelectron spectroscopy.

Guanidine-functionalized particles of the present disclosure include metal silicate particles. Useful metal silicates include silicates of metals such as magnesium, calcium, zinc, aluminum, iron, titanium, and the like (preferably, magnesium, zinc, iron, and titanium; more preferably, magnesium), and combinations thereof. Preferred are amorphous metal silicates in at least partially fused particulate form. In certain embodiments, more preferred are amorphous, spheroidized metal silicates; and even more preferably, amorphous, spheroidized magnesium silicate. In certain embodiments, more preferred are amorphous aluminum silicates. Metal silicates are known and can be chemically synthesized by known methods or obtained through the mining and processing of raw ores that are naturally-occurring.

The metal silicate particle, and more particularly, a magnesium silicate particle, bears sufficient surface hydroxyl groups (typically, Si—OH groups) to enable a desired number of guanidine-containing ligands to be covalently attached thereto.

Amorphous, at least partially fused particulate forms of metal silicate can be prepared by any of the known methods of melting or softening relatively small feed particles (for example, average particle sizes up to about 25 micrometers) under controlled conditions to make generally ellipsoidal or spheroidal particles (that is, particles having magnified two-dimensional images that are generally rounded and free of sharp corners or edges, including truly or substantially circular and elliptical shapes and any other rounded or curved shapes). Such methods include atomization, fire polishing, direct fusion, and the like. A preferred method is flame fusion, in which at least partially fused, substantially glassy particles are formed by direct fusion or fire polishing of solid feed particles (for example, as in the method described in U.S. Pat. No. 6,045,913 (Castle et al.). Most preferably, such methods can be utilized to produce amorphous, spheroidized metal silicates by converting a substantial portion of irregularly-shaped feed particles (for example, from about 15 to about 99 volume percent; preferably, from about 50 to about 99 volume percent; more preferably, from about 75 to about 99 volume percent; most preferably, from about 90 to about 99 volume percent) to generally ellipsoidal or spheroidal particles.

Some amorphous metal silicates are commercially available. For example, amorphous, spheroidized magnesium silicate is commercially available for use in cosmetic formulations (for example, "3M COSMETIC MICROSPHERES CM-111", available from 3M Company, St. Paul, Minn.). 3M COSMETIC MICROSPHERES CM-111 have a particle density of 2.3 g/cc, a surface area of 3.3 m$^2$/g, and have a particle size of: 90 percent less than 11 microns (i.e., $D_{90}$=11), 50 percent less than 5 microns, and 10 percent less than 2 microns. Amorphous aluminum silicate is commercially available for use in paints, primers, powder coatings, and other coatings, for example, "3M CERAMIC MICROSPHERES" from 3M Company, St. Paul, Minn. The 3M CERAMIC MICROSPHERES are alkali alumino silicate ceramic microspheres shaped as solid spheres with particle density of 2.4 g/cc, and are commercially available in three grades: W-210, W-410, and W0610. W-210 particles have a surface area of 5 m$^2$/cc and a particle size of: 95 percent less than about 12 microns (i.e., $D_{95}$=12), 90 percent less than about 9 microns, 50 percent less than about 3 microns, and 10 percent less than about 1 micron. W-410 particles have a surface area of 3 m$^2$/cc and a particle size of: 95 percent less than about 24 microns (i.e., $D_{95}$=24), 90 percent less than about 15 microns, 50 percent less than about 4 microns, and 10 percent less than about 1 micron. W-610 particles have a surface area of 3 m$^2$/cc and a particle size of: 95 percent less than about 40 microns (i.e., $D_{95}$=40), 90 percent less than about 28 microns, 50 percent less than about 10 microns, and 10 percent less than about 1 micron.

The guanidine-functionalized metal silicate particles used in making the nonwoven article of the present disclosure can be used in essentially any particulate form (preferably, a relatively dry or volatiles-free form) that is amenable to blending with fibers to form the nonwoven articles of the present disclosure.

Preferably, the guanidine-functionalized metal particles are used in the form of a powder. Useful powders include those that comprise microparticles (preferably, microparticles having a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 15 or 20 micrometers; where any lower limit can be paired with any upper limit of the range, as referenced above).

In some embodiments, particularly preferred are guanidine-functionalized magnesium silicate particles. Suitable guanidine-functionalized magnesium silicate particles for use in carrying out the process of the present disclosure include those that comprise an amorphous magnesium silicate and that have a surface composition having a metal atom to silicon atom ratio greater than 0.01 and less than or equal to about 0.5 (preferably, less than or equal to about 0.4; more preferably, less than or equal to about 0.3; most preferably, less than or equal to about 0.2), as determined by X-ray photoelectron spectroscopy ("XPS", also known as Electron Spectroscopy for Chemical Analysis ("ESCA")).

In some embodiments, particularly preferred are guanidine-functionalized aluminum silicate particles. Suitable guanidine-functionalized aluminum silicate particles for use in carrying out the process of the present disclosure include those that comprise an amorphous aluminum silicate and that have a surface composition having a metal atom to silicon atom ratio greater than 6.7 and less than or equal to about 17.3, as determined by XPS (also known as ESCA).

XPS is a technique that can provide information about the elemental and chemical (oxidation state and/or functional group) concentrations present on a solid surface. XPS typically provides an analysis of the outermost 3 to 10 nanometers (nm) of the specimen surface. XPS is sensitive to all elements in the periodic table except hydrogen and helium with detection limits for most species in the 0.1 to 1 atomic percent concentration range. In some cases, for example for CM-111 particles, a preferred surface composition assessment conditions for XPS can include a take-off angle of 90 degrees measured with respect to the sample surface with a solid angle of acceptance of ±10 degrees. A person skilled in the art can select a suitable instrument setting for analysis of particles of the present disclosure.

In embodiments of the present disclosure, guanidine-functionalized metal silicate particles have a surface nitrogen content in a range from 1 atomic percent to 20 atomic percent, as measured by XPS. In some embodiments, the guanidine-functionalized metal silicate particles have a surface nitrogen content of at least 1 atomic percent, at least 2, at least 3, at least 4, or even at least 5 atomic percent, as measured by XPS. In some embodiments, the guanidine-functionalized metal silicate particles have a surface nitrogen content of up to 20 atomic percent, up to 15, up to 10, up to 9, up to 8, up to 7, or even up to 6 atomic percent, as measured by XPS. The surface nitrogen content of the guanidine-functionalized metal silicate particles, as measured by XPS, may be any combination of these lower and upper values, inclusive of the values thereof. A person skilled in the art would understand that in some embodiments it may be preferred to select higher or lower surface nitrogen content within these ranges, depending on the desired application.

It will be appreciated that a guanidine group as described herein may be uncharged or charged (e.g., protonated) depending on the particular environment in which it is placed (e.g., depending on the pH of an aqueous buffer with which the guanidine-functionalized particle is brought into contact). In environments in which a guanidine group of a guanidine-functionalized particle is charged, the charged guanidine group may comprise an associated counterion. In some embodiments such a counterion may arise in the generation of the guanidine group (that is, the guanidine group as produced in the synthesis reaction may be charged, and may have a counterion associated therewith, as discussed later herein). In other embodiments a counterion may not arise in the generation of the guanidine group (e.g., the guanidine group may be produced in the synthesis reaction as a free base), but the guanidine-containing ligand (e.g., the functionalized particle) may be later placed into an environment (e.g., a liquid buffer) in which the guanidine group becomes charged and a corresponding counterion becomes associated therewith. In still other embodiments, a particular counterion may be associated with the guanidine group (e.g. as synthesized), but the counterion may then be exchanged for a different counterion. The charge state of a guanidine group and the presence and identity and charge state of a counterion thus possibly varying with environment, it is emphasized that all references to guanidine groups in the claims herein, are irrespective of the charge state of the guanidine group and are irrespective of the presence or identity of an associated counterion, unless such charge state and/or presence and/or identity of a counterion is explicitly specified in the claim.

Furthermore, the concept of a counterion that is associated with a guanidine group is used broadly herein, and it will be understood that such a counterion may not necessarily be constantly located in close proximity to the same guanidine group. Furthermore, the guanidine group and the associated counterion do not necessarily have to always be fully solvated (e.g., in aqueous solution). That is, they may be present as salts in a partially or substantially dried product (e.g., a solid or semi-solid product), which product may be placed into a liquid (e.g., an aqueous buffer) and solvated as desired. In specific embodiments, the associated counterion is a sulfate and/or bisulfate ion. In other specific embodiments, the associated counterion is a hydroxide ion (as may result, for example, from putting a guanidine group in the free-base form into an unbuffered aqueous solution).

In some embodiments, a guanidine-functionalized particle can be made by a simple and convenient method using an O-alkylisourea, or a salt thereof (for example, O-methylisourea hemisulfate, which is a readily available starting material, CAS No. 52328-05-9). In a first step of this method, an O-alkylisourea may be reacted with a linker molecule of the general structure shown in Formula 5:

Formula 5

In Formula 5, Si is a silicon atom, and $NH_2$ denotes a primary amino group. Y is a divalent group that is covalently bonded to the silicon atom at one end and to the primary amino group at the other end. Each $R^a$ group, if any are present, is independently an alkyl, aralkyl, or aryl group, and is attached to the silicon atom (noting that no $R^a$ group will be present when n is 0). Each X is a leaving group covalently bonded to the silicon atom and is independently alkoxy or acyloxy, and n is 0, 1, or 2.

In some embodiments, Y is a divalent alkylene group. A typical alkylene can be up to 20, up to 16, 12, 10, 8, 7, 6, 5, 4, or even up to 3 carbons, or even 2 carbons. In some embodiments, Y is a divalent group comprising an alkylene of 3 to 6 carbons. In a preferred embodiment, Y is a divalent group having 3 carbons (i.e., propyl), as shown, for example in the preferred linker compound of Formula 6.

Formula 6

In some embodiments, a first step of a method of making a guanidine-functionalized metal silicate particle is shown in Reaction Scheme 1, reacting a compound of Formula 5 with an O-alkylisourea (R' can be methyl or other lower alkyl, including anywhere from 2 to 10 carbons). The reaction can be carried out in a suitable solvent (e.g., methanol or ethanol).

Reaction Scheme I

In a more specific embodiment of Reaction Scheme I, the compound of Formula 6 is reacted with an O-methylisourea salt, as shown in Reaction Scheme II.

Reaction Scheme II

In Reaction Scheme II, O-methylisourea is provided as a hemisulfate, and is reacted with 3-aminopropyltrimethoxysilane (in methanol) to form the guanidine group (noting that the charge state of the guanidine group and of the associated hemisulfate counterion are not shown in Reaction Scheme II).

It will be appreciated that Formula 6 and Reaction Scheme II are representative examples and that any suitable linker molecule can be used (as long as the linker molecule includes, e.g., a primary amine that can be reacted with the O-methylisourea to form a guanidine group), within the overall boundaries prescribed herein. For example, the linker molecule can comprise any desired number of any suitable reactive groups (e.g., ethoxy, methoxy, acetoxy) on the silicon atom (noting that if multiple reactive groups are present they do not have to be identical; further noting that if less than three such reactive groups are used, other (e.g., $R^a$) groups can be present, e.g. as shown in the general representation of Formula 4, and still further noting that if multiple $R^a$ groups are present they do not have to be identical). In a specific example, 3-aminopropyltriethoxysilane may be used as the linker molecule rather than the 3-aminopropyltrimethoxysilane of Formula 6 and included in Reaction Scheme II.

In some embodiments, Y is a divalent group comprising an alkylene, and the divalent group can further optionally comprise other groups, including an arylene, oxy, —NH—, or a combination thereof. In some specific embodiments, the divalent Y group of the linker molecule may comprise a secondary amine. In a particular example of this type, the linker molecule may be e.g. N-(2-aminoethyl)-3-aminopropyltrimethoxysilane (available under the trade designation "SIA0591.0" from Gelest, Inc., Tullytown, Pa.). Other potentially useful linker molecules may include e.g. (aminoethylaminomethyl) phenethyltrimethoxysilane ("SIA0588.0", Gelest), N-(2-aminoethyl)-3-aminopropylmethyldimethoxysilane ("SIA0589.0", Gelest), N-(6-aminohexyl) aminopropyltrimethoxysilane ("SIA0594.0", Gelest), N-(2-aminoethyl)-11-aminoundecyl-trimethoxysilane ("SIA0595.0", Gelest), N-3 [(amino(polypropyleneoxy)] aminopropyltrimethoxysilane ("SIA0599.4", Gelest), 3-aminopropylmethyldiethoxysilane ("SIA0605.0", Gelest), 3-aminopropyltriethoxysilane ("SIA0610.0", Gelest), and (3-trimethoxysilylpropyl)diethylene-triamine ("SIT8398.0", Gelest). Mixtures of any of the herein-mentioned linker molecules may be used if desired.

In a second step of this method, at least one of the Si-bonded X groups of the linker molecule (with Si atoms comprising one or more such reactive alkoxy or acyloxy groups being well known by the term silane coupling agents) is reacted with a hydroxyl group of a suitable particle to form a covalent bond between the linker molecule and the particle. (It is emphasized that the terminology of "first" and "second" steps is used purely for convenience of description and that the steps can be performed in any desired order). For example, any or all of the three trimethoxy reactive groups of the linker molecule in Reaction Scheme II may react with surface hydroxyl groups of the particle. In some embodiments, and as mentioned above, the addition of water in the second step of this method has been observed to result in higher surface nitrogen values as measured by XPS (see Example section). The amount of water added can be in a range from 0 to 5 equivalents ("eq") of water relative to the amount of linker molecule ("equivalents" here refers to "molar equivalents", defined as 1 mole of water for each 1 mole of linker molecule), which can include up to 1 eq, or up to 2 eq, up to 1 eq, up to 0.5 eq, up to 0.25 eq, or even any value in between 0 eq and 5 eq of water, relative the amount of linker molecule.

In one embodiment, the net result of these two steps is summarized in exemplary embodiment in Formula 7 (the circle in Formula 7 represents a metal silicate particle):

Formula 7

The specific exemplary representation of Formula 7 shows the thus-produced guanidine group in a positively charged (e.g., protonated) condition with a negatively charged hemisulfate counterion associated therewith. It will be understood that a guanidine-functionalized particle may be produced in such condition by the above method, but that the charge state of the guanidine group, the presence, identity and/or charge state of a counterion, etc., may be affected thereafter by the environment into which the guanidine-functionalized particle is placed, as discussed above.

The general methods-of-making described above, and materials used therein, may be tailored as desired for particular purposes. Thus, in some embodiments, each thus-formed guanidine-containing ligand on the particle may only have a single guanidine group (rather than there being e.g. two, three or more guanidine groups on a given guanidine-containing ligand). In some embodiments, the thus-formed guanidine-comprising ligands may be the only ligands on the particle (rather than there being additional ligands, e.g. silane-coupled ligands, on the particle, which additional ligands do not comprise a guanidine group). In some embodiments, a substantial amount (e.g., an amount readily detectable by surface analysis) of residual hydroxyls are present on the surface of the particle even after the attachment of the linker molecules to some of the hydroxyls of the particle to form ligands thereon (e.g., rather than the residual hydroxyls being endcapped). In some embodiments, the methods disclosed herein do not include a step of equilibrating the particle in an atmosphere having a defined relatively humidity (e.g., of less than 40%) prior to the reacting of the linker molecule with a surface hydroxyl group of the particle.

While the method outlined in Reaction Scheme II uses an O-methylisourea, it will be appreciated that other starting materials might be used to make a guanidine-functionalized linker of the general structure of Formula 1. Such starting materials might include e.g. O-alkylisourea salts such as O-methylisourea sulfate, O-methylisourea hydrogen sulfate, O-methylisourea acetate, O-ethylisourea hydrogen sulfate, and O-ethylisourea hydrochloride. Beyond these materials, other starting materials that might be used to make a guanidine-functionalized linker of the general structure of Formula 1 might include e.g. cyanamide, chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride. It will be appreciated that some of these starting materials may produce a guanidine-containing linker in which the guanidine group is in a specific charge state (e.g., is a free base or is positively charged) and/or has a specific counterion associated therewith. It will be understood that such a guanidine group may be placed into a specific charge state, may have its associated counterion exchanged for some other counterion, and so on, based on the disclosures herein.

Nonwoven articles of the present disclosure include those that comprise (a) a porous fibrous nonwoven matrix and (b) a plurality of the above-described guanidine-functionalized metal silicate particles, the particles being enmeshed in the porous fibrous nonwoven matrix. Preferably, the guanidine-functionalized metal silicate particles are guanidine-functionalized magnesium silicate particles or guanidine-functionalized aluminum silicate particles. Such nonwoven articles can be prepared by essentially any process that is capable of providing a fibrous nonwoven matrix (that is, a web or medium, other than a woven or knitted fabric, comprising interlaid fibers) having the particles enmeshed therein. Useful processes include meltblowing, spunbonding, and other air laying techniques; carding; wet laying; and the like; and combinations thereof (preferably, air laying, wet laying, and combinations thereof; more preferably, wet laying).

Fibers that are suitable for use in preparing the porous fibrous nonwoven matrix of a nonwoven article of the present disclosure include pulpable fibers. Preferred pulpable fibers are those that are stable to radiation and/or to a variety of solvents. Useful fibers include polymeric fibers, inorganic fibers, and combinations thereof (preferably, polymeric fibers and combinations thereof). Preferably, at least some of the fibers that are utilized exhibit a degree of hydrophilicity.

Suitable polymeric fibers include those made from natural (animal or vegetable) and/or synthetic polymers, including thermoplastic and solvent-dispersible polymers. Useful polymers include wool; silk; cellulosic polymers (for example, cellulose, cellulose derivatives, and the like); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; polyolefins (for example, poly(ethylene), poly(propylene), poly(l-butene), copolymers of ethylene and propylene, alpha olefin copolymers such as copolymers of ethylene or propylene with 1-butene, 1-hexene, 1-octene, and 1-decene, poly(ethylene-co-1-butene), poly(ethylene-co-1-butene-co-1-hexene), and the like); poly(isoprenes); poly(butadienes); polyamides (for example, nylon 6; nylon 6,6; nylon 6,12; poly(iminoadipoyliminohexamethylene); poly(iminoadipoyliminodecamethylene); polycaprolactam; and the like); polyimides (for example, poly(pyromellitimide) and the like); polyethers; poly(ether sulfones) (for example, poly(diphenylether sulfone), poly(diphenylsulfone-co-diphenylene oxide sulfone), and the like); poly(sulfones); poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl esters); poly(vinyl ethers); poly(vinyl alcohols); polyaramids (for example, para-aramids such as poly(paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); poly(carbonates); and the like; and combinations thereof. Preferred polymeric fibers include polyamides, polyolefins, polysulfones, and combinations thereof (more preferably, polyamides, polyolefins, and combinations thereof; most preferably, nylons, poly(ethylene), and combinations thereof).

Suitable inorganic fibers include those that comprise at least one inorganic material selected from glasses, ceramics, and combinations thereof. Useful inorganic fibers include fiberglasses (for example, E-glass, S-glass, and the like), ceramic fibers (for example, fibers made of metal oxides (such as alumina), silicon carbide, boron nitride, boron carbide, and the like), and the like, and combinations thereof. Useful ceramic fibers can be at least partially crystalline (exhibiting a discernible X-ray powder diffraction pattern or containing both crystalline and amorphous (glass) phases). Preferred inorganic fibers include fiberglasses and combinations thereof.

The fibers used to form the porous fibrous nonwoven matrix can be of a length and diameter that can provide a matrix having sufficient structural integrity and sufficient porosity for a particular application (for example, for a particular type of sample matrix). For example, lengths of at least about 0.5 mm, 1 mm, 2 mm, 3 mm, 4 mm, 6 mm, 8 mm, 10 mm, 15 mm, 20 mm, 25 mm, or even 30 mm (and combinations thereof), and diameters of at least about 10 micrometers, 20 micrometers, 40 micrometers, or even 60 micrometers (and combinations thereof) can be useful. Preferred fiber lengths and diameters will vary, depending upon factors including the nature of the fiber and the type of application. For example, fibrillated poly(ethylene) can be useful in lengths of about 1 mm to about 3 mm, and non-fibrillated nylon can be useful in lengths of about 6 mm to about 12.5 mm, for a variety of sample matrices.

To facilitate entrapment of the particles and/or to ensure a high surface area matrix, the fibers used to form the porous fibrous nonwoven matrix preferably comprise at least one fibrillated fiber (for example, in the form of a main fiber surrounded by many smaller attached fibrils). The main fiber generally can have a length in the range of about 0.5 mm to about 4 mm and a diameter of about 1 micrometer to about 20 micrometers. The fibrils typically can have a submicrometer diameter.

The porous fibrous nonwoven matrix can comprise two, three, four, or even more different types of fibers. For example, a nylon fiber can be added for strength and integrity, while fibrillated polyethylene can be added for entrapment of the particulates. If fibrillated and non-fibrillated fibers are used, generally the weight ratio of fibrillated fibers to non-fibrillated fibers can be at least about 1:2, 1:1, 2:1, 3:1, 5:1, or even 8:1. Regardless of the type(s) of fibers chosen, the amount of fiber in the resulting nonwoven article (in dry form) is preferably at least about 10, 12, 12.5, 14, 15, 18, 20, or even 22 percent by weight up to about 20, 30, 40, 50, 60, 70, or even 80 percent by weight (based upon the total weight of all components of the nonwoven article).

Preferably, the porous fibrous nonwoven matrix further comprises at least one polymeric binder. Suitable polymeric binders include natural and synthetic polymeric materials that are relatively inert (exhibiting little or no chemical interaction with either the fibers or the guanidine-functionalized metal silicate particles). Useful polymeric binders include polymeric resins (for example, in the form of powders and latexes), polymeric binder fibers, and the like, and combinations thereof. For some applications, polymeric binders can include polymeric binder fibers and combinations thereof. For other applications, polymeric resins and combinations thereof can be preferred polymeric binders.

Suitable polymeric resins for the polymeric binder can include, but are not limited to, natural rubbers, neoprene, styrene-butadiene copolymers, acrylate resins, polyvinyl chloride, polyvinyl acetate, and the like, and combinations thereof. Preferred polymeric resins include acrylate resins and combinations thereof. Suitable polymeric binder fibers can include adhesive-only type fibers (for example, "KODEL 43UD" fibers, available from Eastman Chemical Products, Kingsport, Tenn.), bicomponent fibers (for example, side-by-side forms such as "CHISSO ES" polyolefin thermally bonded bicomponent fibers, available from Chisso Corporation, Osaka, Japan; sheath-core forms such as "MELTY FIBER TYPE 4080" bicomponent fibers having a polyester core and a polyethylene sheath, available from Unitika Ltd., Osaka, Japan; and the like), and the like, and combinations thereof. Preferred polymeric binder fibers include bicomponent fibers and combinations thereof (more preferably, sheath-core bicomponent fibers and combinations thereof).

Regardless of the type of polymeric binder used, the amount of binder in the resulting nonwoven article (in dry form) can be from about 3 weight percent to about 7 weight percent including about 5 weight percent, based upon the total weight of all components of the nonwoven article. Such amounts of polymeric binder generally can provide the porous fibrous nonwoven matrix with sufficient integrity for use in many applications, while not significantly coating the particles. Surprisingly, the amount of polymeric binder in the nonwoven article can be less than about 5, 4, 3, 2, or even 1 percent by weight, relative to the weight of the fibers in the nonwoven article.

Nonwoven articles of the present disclosure can be prepared by a process comprising (a) providing a plurality of the above-described fibers; (b) providing a plurality of the above-described guanidine-functionalized metal silicate particles; and (c) forming at least a portion of the plurality of fibers into a porous fibrous nonwoven matrix having at least a portion of the plurality of particles enmeshed therein. As mentioned above, the forming can be carried out by essentially any process that is capable of providing a fibrous nonwoven matrix (that is, a web or medium, other than a woven or knitted fabric, comprising interlaid fibers) having the guanidine-functionalized metal silicate particles enmeshed therein. Useful processes include meltblowing, spunbonding, and other air laying techniques; carding; wet laying; and the like; and combinations thereof (preferably, air laying, wet laying, and combinations thereof more preferably, wet laying).

Preferably, the forming is carried out by using a wet laying or "wetlaid" process comprising (a) forming a dispersion comprising the plurality of fibers, the plurality of particles (which can be added and dispersed along with the other components prior to carrying out other process steps or, if desired, can be added and dispersed later in the process but generally prior to removal of dispersing liquid), and at least one polymeric binder in at least one dispersing liquid (preferably, water); (b) at least partially depositing the polymeric binder onto at least a portion of the fibers; and (c) removing the dispersing liquid from the dispersion. In such a process, the fibers can be dispersed in the dispersing liquid to form a slurry. If desired, the fibers can comprise additives or chemical groups or moieties to assist in their dispersion. For example, polyolefin-based fibers can comprise maleic anhydride or succinic anhydride functionality, or, during the melt-processing of polyethylene fibers, a suitable surfactant can be added.

Deposition of the polymeric binder onto the fibers can be carried out either before or after the dispersing liquid removal or dewatering step, depending upon the nature of the polymeric binder. For example, when a polymeric latex is used as the polymeric binder, the polymeric latex can be precipitated onto the fibers before or after particle addition and prior to dewatering. After the dewatering, heat can be applied to finish the dewatering and to set the resulting deposited latex. When polymeric binder fibers are used as the polymeric binder, dewatering can generally be carried out first, followed by heating to finish the dewatering and to melt the polymeric binder fibers (and thereby deposit polymeric binder on the fibers).

One or more adjuvants or additives can be used in preparing the nonwoven article. Useful adjuvants include process aids (for example, precipitation agents such as sodium aluminate and aluminum sulfate, which can aid in precipitating the polymeric binder onto the fibers), materials that can enhance the overall performance of the resulting nonwoven article, and the like. When used, the amounts of such adjuvants can range from more than zero up to about 2 weight percent (preferably, up to about 0.5 weight percent; based upon the total weight of the components of the nonwoven article), although their amounts are preferably kept as low as possible so as to maximize the amount of particles that can be included.

In a preferred wetlaid process, the fibers (for example, chopped fibers) can be blended in a container in the presence of the dispersing liquid (for example, water, a water-miscible organic solvent such as an alcohol, or a combination thereof). The amount of shear used to blend the resulting mixture has not been found to affect the ultimate properties of the resulting nonwoven article, although the amount of shear introduced during blending is preferably relatively high. Thereafter, the particles, the polymeric binder, and an excess of a precipitation agent (for example, a pH adjusting agent such as alum) can be added to the container.

When the preferred wetlaid process is carried out by using hand-sheet methods known in the art, the order of addition of the three ingredients to the fiber dispersion has not been found to significantly affect the ultimate performance of the nonwoven article. In some embodiments, addition of the polymeric binder after addition of the particles, however, can provide a nonwoven article exhibiting somewhat greater adhesion of the particles to the fibers. When the preferred wetlaid process is carried out by using a continuous method, the three ingredients preferably are added in the listed order. (The following description is based on a hand-sheet method, although those skilled in the art can readily recognize how to adapt such a method to provide for a continuous process.)

After the particles and the polymeric binder are added to the fiber-liquid slurry, the resulting mixture can be poured into a mold, the bottom of which can be covered by a screen. The dispersing liquid (preferably, water) can be allowed to drain from the mixture (in the form of a wet sheet) through the screen. After sufficient liquid has drained from the sheet, the wet sheet generally can be removed from the mold and dried by pressing, heating, or a combination of the two. Generally pressures of about 300 kPa to about 600 kPa and temperatures of about 100° C. to about 200° C. (preferably, about 100° C. to about 150° C.) can be used in these drying processes. When polymeric binder fibers are used as the polymeric binder in the preferred wetlaid process, no precipitation agent is needed, and the applied heat can be used to melt the polymeric binder fibers.

The resulting dry sheet can have an average thickness of at least about 0.2, 0.5, 0.8, 1, 2, 4, or even 5 mm up to about 5, 8, 10, 15, or even 20 mm. Up to about 100 percent of the dispersing liquid can be removed (preferably, up to about 90 percent by weight). Calendering can be used to provide additional pressing or fusing, if desired.

As mentioned above, the guanidine-functionalized metal silicate particles can be microparticles. The microparticles can be entrapped in the porous fibrous nonwoven matrix through either chemical interactions (for example, chemical bonding) or physical interactions (for example, adsorption or mechanical entrapment), depending upon the nature of the fibers that are utilized. Preferred embodiments of nonwoven articles of the present disclosure include those comprising at least one fibrillated fiber that can effect mechanical entrapment of the guanidine-functionalized metal silicate particles.

Since the capacity and efficiency of a nonwoven article of the present disclosure can vary according to the amount of guanidine-functionalized metal silicate particles contained therein, relatively high particle loadings generally can be desirable. The particles are entrapped in the porous fibrous nonwoven matrix and preferably distributed within it (more preferably, the particles are distributed essentially uniformly throughout the matrix). In some embodiments, the amount of particles in the nonwoven article preferably can be at least about 5, 10, 15, 20, 25, 30 or even 40 weight percent (based upon the total weight of all components of the nonwoven article). In some embodiments, the amount of particles in the nonwoven article preferably can be up to about 90, 80, 70, 60 or even 50 weight percent (based upon the total weight of all components of the nonwoven article). In some embodiments, the amount of particles in the nonwoven article can be in a range from 5 to 90 weight percent, from 10 to 80 weight percent, or even from 20 to 70 weight percent, (based upon the total weight of all components of the nonwoven article), or any combination of the lower and upper limits, including any value between these lower and upper limits.

Generally the average pore size of the sheet material can be in the range of about 0.1 to about 10 micrometers, as measured by scanning electron microscopy ("SEM"). Void volumes in the range of about 20 to about 80 volume percent can be useful (preferably, about 40 to about 60 volume percent). The porosity of the sheet materials can be modified (increased) by including fibers of larger diameter or stiffness in the fiber mixture.

The sheet material can be flexible (for example, able to be rolled around a 0.75 inch (about 2 cm) diameter core). This flexibility can enable the sheet material to be pleated or rolled. The sheet material can have a relatively low back pressure (meaning that a relatively high volume of liquid can be relatively quickly passed through it without generating relatively high back pressure). (As used herein, "relatively low back pressure" may refer to a differential back pressure of less than about 3 pounds per square inch (20.7 kPa), 2.5 (17.2), or 2 (13.8) pounds per square inch (6.9 kPa) at a face velocity from about 7.5 to 11.5 centimeters/second, although none of these backpressure values or face velocities is a requirement.)

The uncalendered sheet material can be cut to a desired size and used to carry out the microorganism removal process of the present disclosure. If desired (for example, when a significant pressure drop across the sheet is not a concern), the sheet material can be calendered to increase its tensile strength prior to use. When the sheet material is to be pleated, drying and calendering preferably can be avoided.

In some embodiments a single layer of sheet material can be effective in carrying out the method of the present disclosure for removing microorganism. Multiple layers can be used, if desired, to provide greater removal capacity.

A significant advantage of the porous fibrous nonwoven matrix of the nonwoven article is that very small guanidine-functionalized metal silicate particle sizes (10 micrometers or smaller) and/or guanidine-functionalized metal silicate particle with a relatively broad size distribution can be employed. This allows for excellent one-pass kinetics, due to increased surface area/mass ratios. Because of the relatively low pressure drops, a minimal driving force (such as gravity or a vacuum) can be used to pull a sample through the nonwoven article, even when small guanidine-functionalized metal silicate particle sizes are employed.

The disclosure includes a method of removing microorganisms from an aqueous sample, using nonwoven articles of the present disclosure. The aqueous sample can be provided from a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility, an industrial facility, soil, a water source, a food preparation area (food contact and non-contact areas), or a laboratory. Food processing, handling, and preparation area samples are preferred, as these are often of particular concern in regard to food supply contamination by bacterial pathogens.

Samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is at least a fluid (for example, a liquid, a gas, or a dispersion or suspension of solid or liquid in liquid or gas).

Examples of samples that can be used include foods (for example, fresh produce or ready-to-eat lunch or "deli" meats), beverages (for example, juices or carbonated beverages), water (including potable water), and biological fluids (for example, whole blood or a component thereof such as plasma, a platelet-enriched blood fraction, a platelet concentrate, or packed red blood cells; cell preparations (for example, dispersed tissue, bone marrow aspirates, or vertebral body bone marrow); cell suspensions; urine, saliva, and other body fluids; bone marrow; lung fluid; cerebral fluid; wound exudate; wound biopsy samples; ocular fluid; spinal fluid; and the like), as well as lysed preparations, such as cell lysates, which can be formed using known procedures such as the use of lysing buffers, and the like. Preferred samples include foods, beverages, water, biological fluids, and combinations thereof (with foods, beverages, water, and combinations thereof being more preferred, and with water being most preferred).

Sample volume can vary, depending upon the particular application. For example, for a diagnostic or research application, the volume of the sample can typically be in the microliter range (for example, 10 microliters or greater). When a filtering process is used for a food pathogen testing assay or for potable water safety testing, the volume of the sample can typically be in the milliliter to liter range (for example, 100 milliliters to 3 liters). In industrial or residential applications, the volume can be tens of thousands of liters.

The process of the present disclosure can be carried out by any of various known or hereafter-developed methods of providing contact between two materials. For example, the nonwoven article can be added to the sample, or the sample can be added to the nonwoven article. The nonwoven article can be immersed in a sample, a sample can be poured onto the nonwoven article, a sample can be poured into a tube or well containing the nonwoven article, or, preferably, a sample can be passed over or through (preferably, through) the nonwoven article (or vice versa). Preferably, the contacting is carried out in a manner such that the sample passes through at least one pore of the porous fibrous nonwoven matrix (preferably, through at least one through pore).

The nonwoven article and the sample can be combined (using any order of addition) in any of a variety of containers or holders (optionally, a capped, closed, or sealed container; preferably, a column, a syringe barrel, or another holder designed to contain the nonwoven article with essentially no sample leakage). Suitable containers for use in carrying out the process of the present disclosure will be determined by the particular sample and can vary widely in size and nature. For example, the container can be small, such as a 10 microliter container (for example, a test tube or syringe) or larger, such as a 100 milliliter to 3 liter container (for example, an Erlenmeyer flask or an annular cylindrical container).

The container, the nonwoven article, and any other apparatus or additives that contact the sample directly can be sterilized (for example, by controlled heat, ethylene oxide gas, or radiation) prior to use, in order to reduce or prevent any contamination of the sample that might cause detection errors. The amount of guanidine-functionalized metal silicate particle in the nonwoven article that is sufficient to provide successful removal of microorganisms of a particular sample will vary and can be readily determined by one skilled in the art.

In an embodiment of the present disclosure, a filtration device includes a container having inlet and outlet ports for liquid passage, and a nonwoven article of the present disclosure contained within the container.

Contacting can be carried out for a desired period (for example, for sample volumes of several liters or for processes involving multiple passes through the nonwoven article, up to about 60 minutes of contacting can be useful; preferably, about 15 seconds to about 10 minutes or longer; more preferably, about 15 seconds to about 5 minutes; most preferably, about 15 seconds to about 2 minutes). Contact can be enhanced by mixing (for example, by stirring, by shaking, or by application of a pressure differential across the nonwoven article to facilitate passage of a sample through its porous matrix) and/or by incubation (for example, at ambient temperature), which are optional but can be preferred, in order to increase microorganism contact with the nonwoven article.

Preferably, contacting can be effected by passing a sample at least once (preferably, only once) through the nonwoven article (for example, by pumping). Essentially any type of pump (for example, a peristaltic pump) or other equipment for establishing a pressure differential across a sample of the nonwoven article contained in a suitable container having inlet and outlet ports for liquid passage (for example, a syringe or plunger) can be utilized. Useful flow rates will vary, depending upon such factors as the nature of the sample matrix and the particular application.

For example, sample flow rates through the nonwoven article of up to about 100 milliliters per minute or more can be effective. Preferably, for samples such as beverages and water, flow rates of about 10-20 milliliters per minute can be utilized. For pre-filtered or otherwise clarified food samples, flow rates of about 6 milliliters per minute (1.5 milliliters per 15 seconds) can be useful. Longer contact times and slower flow rates can be useful for more complex sample matrices such as ground beef or turkey.

A preferred contacting method includes such passing of a sample through the nonwoven article (for example, by pumping). If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, "TRITON X-100" nonionic surfactant available from Union Carbide Chemicals and Plastics, Houston, Tex.), mechanical abrasion/elution agents (for example, glass beads), adsorption buffers, and the like) can be included in a combination of the nonwoven article and sample during contacting.

The process of the present disclosure can optionally further comprise separating the resulting target cellular analyte-bound nonwoven article (and/or microorganism-bound nonwoven article) and the sample. Separation can be carried out by numerous methods that are well-known in the art (for example, by pumping, decanting, or siphoning a fluid sample, so as to leave the target cellular analyte-bound nonwoven article in the container or holder utilized in carrying out the process). It can also be possible to isolate or separate captured target cellular analytes (e.g., target microorganisms or one or more components thereof) from the nonwoven article after sample contacting (for example, by passing an elution agent or a lysis agent over or through the nonwoven article).

The process of the present disclosure can optionally further comprise detecting the resulting at least one bound microorganism or target cellular analyte. Detection can be carried out by numerous methods that are well-known in the art (for example by culture-based methods, microscopy and other imaging methods, genetic detection methods, immunologic detection methods, bioluminescence-based detection methods, and combinations thereof).

The process of the present disclosure can be carried out manually (for example, in a batch-wise manner) or can be automated (for example, to enable continuous or semi-continuous processing).

Select Embodiments of the Present Disclosure

Various embodiments are provided that include the following items:

Item 1. A guanidine-functionalized metal silicate particle, comprising:
  a metal silicate particle that is modified with at least one silane having the formula wherein:
    n is 0, 1, or 2;
    each $R^a$, if present, is independently an alkyl, aralkyl, or aryl;
    Y is a divalent group comprising an alkylene having 2 to 20 carbons;
    G is a guanidine group of the formula —NH—C(=NH)—$NH_2$; and
    each X is independently alkoxy or acyloxy.

Item 2. The particle of item 1, wherein the divalent group further comprises an arylene, oxy, —NH—, or a combination thereof.

Item 3. The particle of item 1 or item 2, wherein the divalent group is alkylene having 3 to 6 carbons.

Item 4. The particle of any one of items 1 to 3, wherein the guanidine group is the reaction product of a primary amine and an O-methylisourea salt.

Item 5. The particle of any one of items 1 to 4, wherein the metal silicate particle is a magnesium silicate particle.

Item 6. The particle of item 5, wherein the magnesium silicate particle is amorphous.

Item 7. The particle of item 5, wherein the magnesium silicate particle comprises a particle size in a range from 5 to 15 micrometers.

Item 8. The particle of any one of items 1 to 4, wherein the metal silicate particle is an aluminum silicate particle.

Item 9. The particle of item 8, wherein the aluminum silicate particle comprises a $D_{95}$ of 12 or 24.

Item 10. The particle of any one of items 1 to 9, wherein n is 0 or 1, and wherein the silane forms a covalent bond with a second silane having the formula according to item 1.

Item 11. The particle of any one of items 1 to 10, wherein the guanidine-functionalized metal silicate particle has a surface nitrogen content in a range from 1 to 20 atomic percent as measured by XPS.

Item 12. A method of making guanidine-functionalized metal silicate particles, the method comprising:
a) reacting an O-methylisourea salt with a linker comprising the formula wherein:
n is 0, 1, or 2;
each $R^a$, if present, is independently an alkyl, aralkyl, or aryl;
Y is a divalent group comprising an alkylene having 2 to 20 carbons; and
each X is independently alkoxy or acyloxy;
to form a guanidine-functionalized linker; and
b) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

Item 13. The method of item 12, wherein step (b) further comprises adding water to the mixture in an amount ranging from 0.1 to 5 equivalents relative to the amount of the guanidine-functionalized linker.

Item 14. The method of item 12 or item 13, wherein the divalent group further comprises an arylene, oxy, —NH—, or a combination thereof.

Item 15. The method of any one of items 12 to 14, wherein the divalent group is alkylene having 3 to 6 carbons.

Item 16. The method of any one of items 12 to 15, wherein the linker is 3-aminopropyltrimethoxysilane.

Item 17. The method of any one of items 12 to 16, wherein the metal silicate particles are magnesium silicate particles or aluminum silicate particles.

Item 18. The method of item 17, wherein the magnesium silicate particles are amorphous or the aluminum silicate particles are amorphous.

Item 19. The method of any one of items 12 to 18, wherein the guanidine-functionalized metal silicate particles have a surface nitrogen content in a range from 1 to 20 atomic percent as measured by XPS.

Item 20. The method of item any one of items 12 to 19, wherein n is 0 or 1, and wherein the guanidine-functionalized linker forms a covalent bond with a second guanidine-functionalized linker according to step (a) of item 10.

Item 21. A nonwoven article comprising:
a) a porous fibrous nonwoven matrix; and
b) a plurality of guanidine-functionalized metal silicate particles according to any one of items 1 to 11 enmeshed within the porous fibrous nonwoven matrix.

Item 22. The article of item 21, wherein the porous fibrous nonwoven matrix contains the plurality of guanidine-functionalized metal silicate particles in a range of 5 wt. % to 25 wt. % by dry weight, relative to a total dry weight of the nonwoven article.

Item 23. The article of item 21 or item 22, wherein the guanidine-functionalized metal silicate particles have a surface nitrogen value in a range from 1 to 20 atomic percent as measured by XPS.

Item 24. The article of any one of items 21 to 23, wherein the guanidine-functionalized metal silicate particles are guanidine-functionalized magnesium silicate particles or guanidine-functionalized aluminum silicate particles.

Item 25. The article of item 24, wherein the guanidine-functionalized magnesium silicate particles are amorphous.

Item 26. The article of any one of items 21 to 24, wherein the guanidine-functionalized metal silicate particles are guanidine-functionalized aluminum silicate particles.

Item 27. The article of item 26, wherein the guanidine-functionalized aluminum silicate particles are amorphous.

Item 28. The article of any one of items 21 to 27, wherein the porous fibrous nonwoven matrix is formed by a wetlaid process.

Item 29. A method of removing microorganisms, target cellular analytes, or a combination thereof, from an aqueous sample, the method comprising:
(a) providing a nonwoven article according to any one of items 21 to 28;
(b) providing a fluid sample containing at least one microorganism strain or target cellular analyte; and
(c) contacting the fluid sample with the nonwoven article such that at least a portion of the at least one microorganism strain or of the at least one target cellular analyte, or a combination thereof, is removed from the fluid sample.

Item 30. The method of item 29, further comprising detecting the presence of at least one bound microorganism strain or bound target cellular analyte.

Item 31. The method of item 30, wherein the detecting is carried out by a method selected from culture-based methods, microscopy and other imaging methods, genetic detection methods, immunologic detection methods, bioluminescence-based detection methods, and combinations thereof.

Item 32. The method of item any one of items 29 to 31, wherein the contacting comprises passing the fluid sample at least once through the nonwoven article.

Item 33. The method of any one of items 29 to 31, wherein the microorganism strain is selected from strains of bacteria, fungi, protozoans, viruses, bacterial endospores, and combinations thereof.

Item 34. A method of making a nonwoven article according to item 21, the method comprising:
a) providing a plurality of fibers;
b) providing a plurality of guanidine-functionalized metal silicate particles according to any one of items 1 to 11; and
c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix.

Item 35. The method of item 34, wherein fibers in the plurality of fibers comprise polymeric and/or inorganic fibers that can be blended and/or pulped.

Item 36. The method of item 35, wherein the polymeric fibers comprise any of polyethylene, nylon, fiberglass, or combinations thereof.

Item 37. The method of any one of items 34 to 36, further comprising mixing at least one polymeric binder together with the plurality of guanidine-functionalized metal silicate particles and the plurality of fibers.

Item 38. The method of any one of items 34 to 37, wherein the mixing includes forming a nonwoven wetlaid scaffold.

Item 39. A filtration device comprising: (a) a container having inlet and outlet ports for liquid passage; and (b) a nonwoven article according to any one of items 21 to 28 contained within the container.

EXAMPLES

Surface Nitrogen Analysis

Atomic percent surface nitrogen levels of guanidine-functionalized magnesium silicate particles (as a "powder") were measured by X-ray photoelectron spectroscopy ("XPS"; also known as "ESCA"). Samples of the powder were pressed onto double-sided, pressure sensitive adhesive tapes on aluminum foil. Excess powder was removed from each sample surface by blowing with compressed nitrogen gas. Instrument and operating conditions were as summarized in the table immediately below:

| | |
|---|---|
| Instrument | PHYSICAL ELECTRONICS QUANTERA II ™ obtained from <company name, city, state> |
| analysis areas | 500 μm × 1500 μm |
| photoelectron take off angle | 45° 20° solid angle of acceptance |
| x-ray source | Monochromatic Al Kα (1486.6 eV) 85 W |
| charge neutralization | Low energy e− and Ar+ flood sources |
| charge correction | C1s max ~284.8 eV |
| analysis chamber pressure | <3 × $10^{-8}$ Torr (<4 × $10^{-6}$ Pa) |

An area of the surface of the powder measuring about 300 micrometers by about 700 micrometers was analyzed for each data point. Three areas on each sample were analyzed and averaged to obtain the reported average atomic percent values. Data processing was carried out using standard "VISION" software (Kratos Analytical, Manchester, England).

Materials

All chemicals were purchased from Sigma Aldrich/Fischer Scientific unless otherwise noted. Microbiological testing was performed in duplicates with standard deviation less than 10% observed unless otherwise stated.

| | |
|---|---|
| CM-111 | Amorphous, spheroidized magnesium silicate purchased from 3M Company, St. Paul, MN, as "3M COSMETIC MICROSPHERES", CAS No. 1343-88-0. |
| W-210 | Amorphous aluminum silicate purchased from 3M Company, St. Paul, MN, as "3M CERAMIC MICROSPHERES", Grade 210 ($D_{95}$ = 12 microns) |
| W-410 | Amorphous aluminum silicate purchased from 3M Company, St. Paul, MN, as "3M CERAMIC MICROSPHERES", Grade 410 ($D_{95}$ = 24 microns) |
| W-610 | Amorphous aluminum silicate purchased from 3M Company, St. Paul, MN, as "3M CERAMIC MICROSPHERES", Grade 610 ($D_{95}$ = 40 microns) |
| TSA plate | plates prepared according to manufacturer's instructions with 3 wt % "TRYPTIC SOY AGAR POWDER" purchased from BD (DIFCO), Sparks MD |
| TSB | broth prepared according to manufacturer's instructions with 3.7 wt % "TRYPTIC SOY BROTH POWDER" purchased from BD (DIFCO), Sparks MD |
| Endo Agar plate | Premade agar plates, Catalog # 254016, purchased from Becton Dickinson Sparks MD |
| Butterfield's buffer | Monobasic potassium phosphate buffer obtained from 3M Company, St. Paul, MN, as "3M FLIP-TOP DILUTION BOTTLE WITH BUTTERFIELD'S BUFFER" (Catalog Number FTBFD90) |
| DI water | deionized, filtered, 18 megaohm water, processed through "MILLI-Q GRADIENT SYSTEM" obtained from Millipore, Waltham, MA |
| 0.45 micrometer filters | 47 mm cellulose nitrate filters, 0.45 micrometer pore size, from Sartorius obtained from Fisher Scientific |
| Fiber 1 | Short fibrillated polyethylene fibers, obtained from Minifibers, Inc., Johnson City, TN, under the trade designation "SHORT STUFF POLYETHYLENE" |
| Fiber 2 | 6 denier 2 inches long chopped nylon fibers, obtained from Minifibers, Inc., Johnson City, TN |
| Fiber 3 | 1 denier bicomponent ethylene vinyl acetate/polypropylene fibers, obtained from Minifibers, Inc., Johnson City, TN |
| Fiber 4 | long glass fibers, obtained from Schuller, Inc., Denver, CO, under the trade designation "MICRO-STRAND 106-475 GLASS FIBERGLAS" |
| *Escherichia coli* ATCC 11229 | Purchased from American Type Culture Collection, Manassas, VA |

Preparation of 3-Guanidinopropyltrimethoxysilane hemisulfate (as Also Described in U.S. Provisional Patent Application No. 61/733,156, filed on Dec. 4, 2012).

A suspension of O-methylisourea hemisulfate (50.0 g, 0.407 mol) in anhydrous methanol (400 mL) was treated with 3-aminopropyltrimethoxysilane (70.9 mL, 0.407 mol). The reaction mixture was stirred under an atmosphere of nitrogen for 3 days. The reaction mixture was then concentrated under reduced pressure to give 116.8 g of the title compound as a waxy solid. $^1$H NMR analysis ($CD_3OD$, 500 MHz) revealed the following parameters: δ 3.44 (s, 9H), 3.01 (m, 2H), 1.54 (m, 2H), 0.56 (m, 2H).

Preparation of Guanidine-Functionalized CM-111 Particles

A mixture of O-methylisourea hemisulfate (12.9 g, 105 mmol) in anhydrous methanol (100 g) was treated with 3-aminopropyltrimethoxysilane (18.8 g, 105 mmol) and stirred for 2 days, to provide a reagent solution. Next, 12.0 g portions of this reagent solution were transferred to each of five 8 oz. screw cap jars and each sample was diluted with 90 mL of anhydrous methanol. 10.0 g portions of CM-111 (i.e., magnesium silicate) particles were added to each jar, followed by differing amounts of water, as shown in Table 1 (below), as Examples E1-A to E1-E. The jars were sealed with polytetrafluoroethylene-lined caps and the mixture in each jar was stirred for 2 days. The resulting guanidine-functionalized CM-111 samples were isolated by filtration, rinsed with methanol and allowed to air dry, to provide guanidine-functionalized magnesium silicate particles. The amounts of water added and results for ECSA testing (i.e., elements present at a detectable level by XPS on the surface of the guanidine-functionalized magnesium silicate particles, reported as "atomic percent N") and nitrogen combustion analysis ("% N") are summarized in Table 1 below. Unfunctionalized CM-111 particles were tested for atomic percent N by XPS, as Comparative Example CE1.

TABLE 1

| Example No. | Equivalents* of water relative to 3-aminopropyl-trimethoxysilane | Atomic percent N (XPS) | % N (Combustion analysis) | Ratio of atomic percent N to atomic percent Si (XPS) |
|---|---|---|---|---|
| CE1 (CM-111) | N/A | 0 | — | 0 |
| E1-A | 0 | 0.9 | <L.D.** | 0.04 |
| E1-B | 0.25 | 1.5-1.7 | <L.D.** | 0.07 |
| E1-C | 0.5 | 2.8-3.1 | <L.D.** | 0.14 |
| E1-D | 1.0 | 7.3-8.0 | 0.92 | 0.42 |
| E1-E | 2.0 | 8.7-9.0 | 2.21 | 0.53 |

*; **<L.D. = below the limit of detection.

Preparation of Guanidine-Functionalized W-210 Particles

A solution of 3-aminopropyltrimethoxysilane (9.3 g, 51 mol) dissolved in anhydrous methanol (50 mol) was treated with of O-methylisourea hemisulfate (6.3 g, 52 mmol). The reaction mixture was stirred under an atmosphere of nitrogen for 3 days. W-210 particles (50 g) were added to the flask with an additional 200 mL of methanol. The reaction mixture was treated with DI water (0.9 mL, 50 mmol) and stirred for two days to facilitate reaction between the trimethoxysilane and the particles. The resulting guanidine-functionalized W-210 particles were isolated by filtration, rinsed with DI water, followed by methanol, and allowed to air dry. ECSA testing (i.e., elements present at a detectable level by XPS on the surface of the particles of Example E2 and Comparative Example CE2 (unfunctionalized W-210), in triplicate, reported as average "atomic percent N") and nitrogen combustion analysis ("% N") are summarized in Table 2 below.

Preparation of Guanidine Functionalized W-410 Particles

A solution of 3-aminopropyltrimethoxysilane (9.3 g, 52 mmol) dissolved in anhydrous methanol (50 mL) was treated with of O-methylisourea hemisulfate (6.3 g, 51 mmol). The reaction mixture was stirred under an atmosphere of nitrogen for 3 days. W-410 particles (50 g) were added to the flask with an additional 200 mL of methanol. The reaction mixture was treated with DI water (0.9 mL, 50 mmol) and stirred for two days to facilitate reaction between the trimethoxysilane and the particles. The resulting guanidine-functionalized W-410 particles were isolated by filtration, rinsed with DI water, followed by methanol, and allowed to air dry. ECSA testing (i.e., elements present at a detectable level by XPS on the surface of the particles of Example E3 and Comparative Example CE3 (unfunctionalized W-410), in triplicate, reported as average "atomic percent N") and nitrogen combustion analysis ("% N") are summarized in Table 2 below.

Preparation of Guanidine Functionalized W-610 Particles

A solution of 3-aminopropyltrimethoxysilane (9.3 g, 52 mmol) dissolved in anhydrous methanol (50 mL) was treated with of O-methylisourea hemisulfate (6.3 g, 51 mmol). The reaction mixture was stirred under an atmosphere of nitrogen for 3 days. W-610 particles (50 g) were added to the flask with an additional 200 mL of methanol. The reaction mixture was treated with DI water (0.9 mL, 50 mmol) and stirred for two days to facilitate reaction between the trimethoxysilane and the particles. The resulting guanidine-functionalized W-610 particles were isolated by filtration, rinsed with DI water, followed by methanol, and allowed to air dry. ECSA testing (i.e., elements present at a detectable level by XPS on the surface of the particles of Example E4 and Comparative Example CE4 (unfunctionalized W-610), in triplicate, reported as average "atomic percent N") and nitrogen combustion analysis ("% N") are summarized in Table 2 below.

TABLE 2

| Example No. | Atomic percent N (XPS) | Ratio of atomic percent N to atomic percent Si (XPS) |
| --- | --- | --- |
| E2 | 15-16 | 1.36 |
| E3 | 8.1-8.2 | 0.51 |
| E4 | 4.6-4.8 | 0.27 |
| CE2 (W-210) | 0 | 0 |
| CE3 (W-410) | 0-0.1 | 0.01 |
| CE4 (W-610) | 0-0.1 | 0.01 |

Preparation of Nonwoven Articles

Fourteen fiber premixes were prepared by mixing various amounts of Fiber 1 ("F1"), Fiber 2 ("F2"), Fiber 3 ("F3"), and Fiber 4 ("F4") as shown in Table 3 below. Fibers F1-F4 were added in the indicated amounts to 3 liters of cold DI water in a 4 L blender (available from VWR, Radnor, Pa., under the trade designation "WARNING COMMERCIAL HEAVY DUTY BLENDER, MODEL 37BL84") and blended at low speed for 30 seconds. The mixture was examined for uniform dispersion of the fibers without nits or clumps. The additives from the indicated Examples were added with an additional liter of DI water and mixed at low speed for 15 seconds. Comparative Examples were prepared using untreated metal silicate particles (e.g., CM-111 particles, W-210 particles, etc., without any guanidine-functionalization treatment) as the additive.

A felt was prepared using a pad maker apparatus (obtained from Williams Apparatus, Watertown, N.Y., under the trade designation "TAPPI") that had a box measuring about 30 centimeters square and 30 centimeters high with a fine mesh screen at the bottom and a drain valve. On the screen ~a 14 inch (36 centimeters)×12 inch (30 centimeters) piece of a polyethylene spunbond (PET Lutradur 7240 obtained from Fiberweb, Cincinnati, Ohio) was laid as scrim on the screen. The box was filled with tap water up to a height of about 1 centimeter above the screen. Each fiber and additive mixture was poured into the box and the valve was opened immediately which created a vacuum that pulled the water out of the box. The resulting wet-laid felt was approximately 0.8-1 millimeter thick.

The wet-laid felt was transferred from the apparatus onto a 20 centimeter square sheet of blotter paper (96-pound white paper, obtained from Anchor Paper, St. Paul, Minn.). The felt was sandwiched between 2 to 4 layers of blotter paper, to blot excess water. The pressed felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 2.5 to 3 hours to remove residual water and to form a porous wetlaid matrix.

TABLE 3

| | Material | | | | |
| --- | --- | --- | --- | --- | --- |
| Example No. | F1, grams | F2, grams | F3, grams | F4, grams | Additive, grams, of Example No. |
| CE5(CM-111) | 11.00 | 3.00 | 2.25 | 1.76 | 5.10 g of CE1 |
| E5-A | 11.01 | 3.01 | 2.25 | 1.75 | 5.01 g of E1-A |
| E5-B | 11.01 | 3.01 | 2.25 | 1.76 | 5.07 g of E1-B |
| E5-C | 11.01 | 3.01 | 2.25 | 1.76 | 5.10 g of E1-C |
| E5-D | 11.01 | 3.02 | 2.25 | 1.78 | 5.00 g of E1-D |
| E5-E | 11.01 | 3.01 | 2.26 | 1.76 | 5.04 g of E1-E |
| E5-F | 11.03 | 3.02 | 2.26 | 1.76 | 1.32 g of E1-E |
| E5-G | 11.04 | 3.02 | 2.26 | 1.76 | 2.51 g of E1-B |
| CE6 (W-210) | 11.05 | 3.00 | 2.25 | 2.25 | 5.03 g of CE2 |
| E6 | 11.03 | 3.02 | 2.25 | 2.25 | 5.02 g of E2 |
| CE7 (W-410) | 11.08 | 3.02 | 2.24 | 1.74 | 5.03 g of CE3 |
| E7 | 11.07 | 3.01 | 2.26 | 1.76 | 5.00 g of E3 |
| CE8 (W-610) | 11.02 | 3.02 | 2.25 | 1.74 | 5.02 g of CE4 |
| E8 | 11.03 | 3.02 | 2.27 | 1.76 | 5.00 g of E4 |

Preparation of Bacterial Test Samples

A streaked culture of *E coli* (ATCC 11229) on a TSA plate was incubated overnight at 37° C. From the plate an isolated colony was removed and inoculated into 5 mL of TSB using a standard microbiology loop and incubated in a shaking incubator ("INNOVA 44", obtained from New Brunswick Scientific) at 37° C. for 20-22 hours. The overnight culture that contained ~2-3×10$^9$ CFU/mL was serially diluted in Butterfield's Buffer to obtain an inoculum with approximately 1×10$^6$ CFU/mL.

A test sample was prepared by inoculating 200 mL of DI water with a 1:100 dilution of the $10^6$ CFU/mL inoculum resulting in water test sample containing approximately $10^4$ CFU/mL (~4 Log CFUs/ml).

Filtration Testing of Nonwoven Articles

For each of the Examples and Comparative Examples, a disk 47 mm in diameter was die punched from the corresponding wetlaid matrix and placed into a sample holder which was a custom device fabricated from polycarbonate. The device had three parts and was cylindrically shaped measuring about 60 cm in diameter by about 45 cm high. The lower part contained a support screen for the filter disk and a sample outlet port. The top portion was enclosed except for the sample inlet port through PVC tubing connected to the Cole Parmer peristaltic pump and was vented on the upstream side to allow for of purging air. O-ring seals were used to prevent leakage on both the upstream and downstream sides. Internal threads provided closure pressure. The 47 mm disk was placed on top of the support screen, an O-ring was added on top and holder was closed.

The wetlaid matrix was tested in duplicate (except for CE6, which was tested in singlicate). A pre-filtration bacterial test sample was pumped through the sample holder containing the nonwoven matrix disk using a peristaltic pump (available from Cole Parmer, Vernon Hills, Ill., under "MODEL NO. 7553-70") using ⅛ inch (3.2 mm) wall thickness PVC tubing (VWR catalog #60985-522). The spiked water was pumped through the wetlaid matrix at a flow rate of 12 mL/minute. Filtrates were collected in 250 mL sterile glass bottles. The first 100 mL filtrate was collected and discarded. The second 100 mL filtrate was collected for further processing.

Filtrate Testing for the Wetlaids of Examples E5-A to E5-G, E6 to E8, and Comparative Examples CE5 to CE8.

After each filtration test, the holder was disassembled to remove the porous fibrous nonwoven matrix using sterile forceps. Between testing of the porous fibrous nonwoven matrices the filtration device was rinsed with filtered sterilized 500 mL DI water.

For the Comparative Examples (CE9 to CE12) and Examples E10 and E12, a 10 mL volume of the second 100 mL filtrate was added to a 100 mL flip-top bottle containing Butterfield's Buffer to obtain a 1:10 dilution. The bottle was capped and mixed manually by shaking for 10 seconds. A 10 mL volume was removed and added to another flip-top bottle to obtain a 1:100 dilution. Similarly the filtrate was further diluted to 1:1000 and 1:10000. These 100 mL diluted filtrates were vacuum filtered through 0.45 micrometer filters. For Examples E9-A to E9-G and E11, undiluted filtrates were vacuum filtered through 0.45 micron filters.

After each filtration, the vacuum apparatus was rinsed with filtered sterilized 500 mL DI water and blotted dry with laboratory wipes (obtained from Kimberly Clark, Dallas, Tex., under the trade designation "KIMWIPES").

The filters were removed from the apparatus with sterile forceps plates and placed on Endo agar plates, grid side up. The plates were incubated at 37° C. for 18-20 hours. Colony counts were obtained from plates by manual counting. A 10 microliter volume from the pre-filtration sample was added to a 100 mL flip-top bottle containing Butterfield's Buffer, mixed manually by shaking and filtered as the procedure above. The CFU/mL colony counts were converted to Log CFU/mL values.

Log Reduction Values ("LRV") were calculated based on counts obtained from the plated filtrate and pre-filtration samples by using the Equation I below.

$$LRV = (\text{Log of CFUs/mL in pre-filtration sample}) - (\text{Log of CFUs/mL in filtrate sample}) \qquad (I)$$

The Log CFUs in pre-filtration samples and LRV results for filtration of wetlaid matrix Examples E5-A to E5-G, E6-E8, and Comparative Examples CE5 to CE8 are summarized in Table 4.

TABLE 4

| Wetlaid matrix from Example No. | Filtration Example No. | Log CFUs in pre-filtration sample | LRV |
|---|---|---|---|
| CE5 | CE9 (CM-111) | 4.53 | 1.12 |
| E5-A | E9-A | 3.45 | 0.75 |
| E5-B | E9-B | 3.45 | 3.33 |
| E5-C | E9-C | 3.45 | 3.45 |
| E5-D | E9-D | 3.60 | 3.60 |
| E5-E | E9E | 3.60 | 3.60 |
| E5-F | E9F | 4.84 | 4.84 |
| E5-G | E9G | 4.53 | 0.93* |
| CE6 | CE10 (W-210) | 4.53 | 1.77 |
| E6 | E10 | 4.67 | 4.67 |
| CE7 | CE11 (W-410) | 4.1 | 0.19 |
| E7 | E11 | 4.57 | 4.57 |
| CE8 | CE12 (W-610) | 4.1 | 0.21 |
| E8 | E12 | 4.42 | 0.85 |

*A standard deviation of 21% was observed.

Pressure Drop Measurements

A 47 mm disk from the material of Example E6 was die punched. The disk was inserted into a plastic/polycarbonate holder (as described in bacterial filtration testing above). DI water was pumped into the holder using a SCILOG FILTERTEC pump system (Scilog Bioprocessing Systems, Madison, Wis.). A pressure flow cell (SciLog) was inserted between the holder and the pump. The filter holder was connected to the pump system using a MasterFlex tubing #25 (from Cole Parmer). Pressure (in psi) was recorded from the digital display on the pump. One liter of DI water was flushed through the disks at 200 ml/min. Then 1 liter of DI water was pumped through the filter at 200 mL/min and pressure measurements were recorded after a 100 mL volume passed through the filter, for Example E13-A. Filtrates were collected in a plastic beaker. Samples were tested in duplicates. The average pressure drop measurement is shown in Table 5 below.

For Example E13-B, pressure measurements were recorded at 130 mL/min. The only other difference from the pressure drop measurement procedure for Example E13-A was that the sample/filter holder was connected to the pump using a MasterFlex tubing #16 (from Cole Parmer). Samples were tested in duplicates. The average pressure drop measurement is shown in Table 5 below.

TABLE 5

| Example # | Flow rate in mL/min | Ave pressure drop in psi |
|---|---|---|
| E13-A | 200 | 1.74 |
| E13-B | 130 | 1.88 |

What is claimed is:

1. A plurality of guanidine-functionalized metal silicate particles, comprising:
a metal silicate particle that are modified with at least one silane having the formula $$X_{3-n}R^a{}_n Si-Y-G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy, wherein the at least one silane is covalently bonded to each metal silicate particle through at least one oxygen atom,
wherein the plurality of guanidine-functionalized metal silicate particles is in a particulate form,
wherein the guanidine-functionalized metal silicate particles are made by:
a) reacting an O-methylisourea salt with a linker comprising the formula wherein:
n, $R^a$, Y, and X are each as defined above;
to form a guanidine-functionalized linker; and
b) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

2. The particles of claim 1, wherein the divalent group further comprises an arylene, oxy, —NH—, or a combination thereof.

3. The particles of claim 1, wherein the divalent group is alkylene having 3 to 6 carbons.

4. The particles of claim 1, wherein the metal silicate particles are magnesium silicate particles.

5. The particles of claim 1, wherein the metal silicate particles are aluminum silicate particles.

6. The particles of claim 1, wherein the guanidine-functionalized metal silicate particles have a surface nitrogen content in a range from 1 to 20 atomic percent as measured by X-ray photoelectron spectroscopy (XPS).

7. The particles of claim 1, wherein n is 0 or 1, and wherein a silane forms a covalent bond with a second silane having the formula $X_{3-n}R^a{}_n$Si—Y-G, wherein: n, $R^a$, Y, and X are each as defined in claim 1.

8. The particles of claim 1, wherein the particulate form of the plurality of guanidine-functionalized metal silicate particles is a powder.

9. The particles of claim 1, wherein step (b) further comprises adding water to the mixture in an amount ranging from 0.1 to 5 equivalents relative to the amount of the guanidine-functionalized linker.

10. A method of making the guanidine-functionalized metal silicate particles of claim 1, the method comprising:
a) reacting an O-methylisourea salt with a linker comprising the formula wherein:
n is 0, 1, or 2;
each $R^a$, if present, is independently an alkyl, aralkyl, or aryl;
Y is a divalent group comprising an alkylene having 2 to 20 carbons; and
each X is independently alkoxy or acyloxy;
to form a guanidine-functionalized linker; and
b) forming a mixture of the guanidine-functionalized linker and metal silicate particles, such that the guanidine-functionalized linker reacts with hydroxyl groups of the metal silicate particles to form covalent bonds between the guanidine-functionalized linker and the metal silicate particles, thereby forming the guanidine-functionalized metal silicate particles.

11. The method of claim 10, wherein step (b) further comprises adding water to the mixture in an amount ranging from 0.1 to 5 equivalents relative to the amount of the guanidine-functionalized linker.

12. The method of claim 10, wherein the linker is 3-aminopropyltrimethoxy silane.

13. The method of claim 10, wherein the metal silicate particles are magnesium silicate particles or aluminum silicate particles.

14. The method of claim 10, wherein the guanidine-functionalized metal silicate particles have a surface nitrogen content in a range from 1 to 20 atomic percent as measured by XPS.

15. The method of claim 10, wherein n is 0 or 1, and wherein the guanidine-functionalized linker forms a covalent bond with a second guanidine-functionalized linker according to step (a) of claim 10.

16. A nonwoven article comprising:
a) a porous fibrous nonwoven matrix; and
b) a plurality of guanidine-functionalized metal silicate particles according to claim 1 enmeshed within the porous fibrous nonwoven matrix.

17. The article of claim 16, wherein the metal silicate particles are magnesium silicate particles or aluminum silicate particles.

18. A method of removing microorganisms from an aqueous sample, the method comprising:
a) providing a nonwoven article according to claim 16;
b) providing a fluid sample containing at least one microorganism strain; and
c) contacting the fluid sample with the nonwoven article such that at least a portion of the at least one microorganism strain is removed from the fluid sample.

19. The method of claim 18, further comprising detecting the presence of at least one bound microorganism strain.

20. The method of claim 18, wherein the contacting comprises passing the fluid sample at least once through the nonwoven article.

21. A method of making a nonwoven article according to claim 16, the method comprising:
a) providing a plurality of fibers;
b) providing a plurality of guanidine-functionalized metal silicate particles according to claim 1;
c) mixing the plurality of guanidine-functionalized metal silicate particles and the plurality of fibers together to form a porous fibrous nonwoven matrix having the guanidine-functionalized metal silicate particles enmeshed within the porous fibrous nonwoven matrix; and
d) mixing at least one polymeric binder together with the plurality of guanidine-functionalized metal silicate particles and the plurality of fibers.

22. A filtration device comprising:
a) a container having inlet and outlet ports for liquid passage; and
b) a nonwoven article according to claim 16 contained within the container.

* * * * *

UNITED STATES PATENT AND TRADEMARK OFFICE
CERTIFICATE OF CORRECTION

PATENT NO. : 10,914,659 B2
APPLICATION NO. : 14/914017
DATED : February 9, 2021
INVENTOR(S) : Manjiri Kshirsagar et al.

Page 1 of 1

It is certified that error appears in the above-identified patent and that said Letters Patent is hereby corrected as shown below:

In the Specification

Column 13,
Line 16, delete "poly(l-butene)," and insert -- poly(1-butene), --, therefor.

Column 15,
Line 22, delete "thereof" and insert -- thereof; --, therefor.

Column 24,
Line 14, delete "2012)." and insert -- 2012, Attorney Docket No. 70149US002). --, therefor.

Column 26,
Line 3, delete ""WARNING" and insert -- "WARING --, therefor.

In the Claims

Column 28,
Line 65, in Claim 1, before "metal" delete "a".
Line 65, in Claim 1, delete "particle" and insert -- particles --, therefor.

Column 30,
Lines 13 & 14, in Claim 12, delete "3-aminopropyltrimethoxy silane." and insert
-- 3-aminopropyltrimethoxysilane. --, therefor.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*